United States Patent [19]

Leahey et al.

[11] Patent Number: 4,964,410
[45] Date of Patent: Oct. 23, 1990

[54] TIME PERIOD AND HEART RATE MEASUREMENT SYSTEM

[75] Inventors: Edward Leahey, Kemah; Alexander J. Zinner, III, Deer Park; Christopher A. Howard, Houston, all of Tex.

[73] Assignee: Coherent Systems, Inc., Houston, Tex.

[21] Appl. No.: 271,572

[22] Filed: Nov. 15, 1988

[51] Int. Cl.$^5$ .............................................. A61B 5/02
[52] U.S. Cl. .................................... 128/696; 128/710
[58] Field of Search ............... 128/696, 710, 703, 704; 364/413.02, 413.03, 413.04, 413.05, 413.06; 368/89

[56] References Cited

U.S. PATENT DOCUMENTS

| | | | |
|---|---|---|---|
| 3,696,610 | 10/1972 | Charbonnier | 368/89 |
| 3,868,567 | 2/1975 | Ekstrom | 128/704 |
| 4,546,776 | 10/1985 | Bellin et al. | 128/704 |
| 4,630,204 | 12/1986 | Mortara | 364/413.06 |
| 4,742,458 | 5/1988 | Nathans et al. | 364/413.06 |
| 4,831,605 | 5/1989 | Suga | 368/89 |

OTHER PUBLICATIONS

501(k) filing of Coherent Systems, Inc. to the Food and Drug Administration (Jul. 22, 1988).

Primary Examiner—Francis Jaworski
Assistant Examiner—George Manuel
Attorney, Agent, or Firm—Pravel, Gambrell, Hewitt, Kimball & Krieger

[57] ABSTRACT

A system for allowing interactive time measurement and comparison of events and indication of heart rate intervals is disclosed. A part of vertical lines, an anchor bar and a movable or measurement bar, are displayed on a graphic display along with the signal to be analyzed. The bars can be moved relative to each other and the time between the two bars is indicated above a horizontal line connecting the bars. The bars may be locked in place and moved to a different portion of the gathered signals to allow precise comparison. Additionally, a signal channel is monitored for maximum, minimum and baseline values. These values are used to determine a maximum deviation from the baseline and from that deviation an event trigger level is developed. The time between two signal portions greater than the trigger level is measured and displayed as the heart rate.

8 Claims, 13 Drawing Sheets

TIME PERIOD AND HEART RATE MEASUREMENT SYSTEM

COPYRIGHT AUTHORIZATION

A portion of the disclosure of this patent document contains material which is subject to copyright protection. The copyright owner has no objection to the facsimile reproduction by anyone of the patent document or the patent disclosure, as it appears on the Patent and Trademark Office patent file or records, but otherwise reserves all copyright rights whatsoever.

BACKGROUND OF THE INVENTION

1. Field of the Invention

The invention relates to event time period and heart rate measurement, and more particularly, to a user controllable method to measure times between displayed events and to measure heart rate. 2. Description of the Prior Art Cardiac electrophysiology is a subspeciality within the field of cardiology which attempts to study heart rhythm disorders. Heart irregularities can range from occasional extra beats to life threatening fast or slow rhythms. Treatments for these problems include reassurance, drugs, pacemakers, cardiac surgery, electrical ablation of nerve conducting paths in the heart, and implantable automatic defibrillators which can recognize malignant rhythm disorders and produce an electric shock to the heart to terminate the rhythm.

Though most heart rhythm disorders can be treated by non-electrophysiologists, failure of the patient to respond to conventional therapy or presentation of a patient with a malignant rhythm requiring intensive intervention results in referral of the patient to the electrophysiologist. In order to understand the nature of the disorder, the physician will perform an electrophysiological study on the patient. The purpose of the study is to measure the conduction parameters of the heart and to reproduce the rhythm disorder if possible.

The study starts by placing the patient recumbent in a well equipped cardiac laboratory, sedating the patient and placing catheters into various parts of the heart. The catheters are placed by accessing large veins and arteries in the body, puncturing these vessels and then threading the thin catheters, typically having diameters of 2 to 4 mm, into the vessels, guiding the catheters toward the heart while monitoring the catheter position by X-ray, and placing the catheters appropriately within the specific chambers of the heart to be analyzed. The catheters have a number of electrode locations spaced along the end of the catheter to allow various types and locations of electrical measurements to be performed. The electrode leads from the catheter are connected to amplifiers to increase the signal level from the 2-50 mV range to more useable levels. These amplified signals are typically supplied to an oscilloscope for direct observation and to a storage device. The storage devices are typically a magnetic tape unit or a light sensitive paper recording unit. The signals received from the electrodes represent the activation of the heart muscle or the conduction by nerve tissue which carries the activation signal to various parts of the heart in order to excite and thus cause contraction of the heart muscle, resulting in the pumping of blood.

Two to four catheters are placed in a typical study and each catheter may have several electrodes on it, providing typically 2-12 signals to view. Additionally, there are usually 3 or 4 body surface leads attached and simultaneously monitored.

In order to study the conduction controllable characteristics of the heart, one of the catheters is connected to a pacemaker unit which provides pulses of electricity similar to the hearts natural pacemaker. In one type of test, a series of uniformly spaced impulses is provided to cause the heart to pump. An odd impulse is provided a selectable time after a uniformly spaced impulse. If the impulse does not cause a beat, the odd impulse is within the refractory period. A group of these series are performed and the desired drug introduced into the patient. The test protocol is repeated to determine if any changes have occurred because of the drug.

A second type of test uses different impulse waveforms and trigger locations to attempt to get the heart into the malignant rhythm. If this can be done, the various locations, signal types, and timing intervals provide information to identify the problem so that the desired treatment can be performed.

In yet a third test, the heart is paced until a uniform rhythm is obtained, then the pacing signal is stopped. The heart's own pacemaker should take over and begin controlling the pumping. The time interval and various conduction paths identify certain problems which may be treated.

All of the information is recorded during the various tests or protocols. The entire session or study may last from 15 minutes to many hours, with individual test series lasting seconds to minutes. The data which has been recorded must then be analyzed. When the laboratory uses light sensitive paper as the recording medium, as most laboratories do, the physician must use mechanical hand calipers to take the time measurements necessary for proceeding with analysis. The physician must sort through many feet of paper with the hand calipers. This technique is quite cumbersome and takes a significant amount of time if done properly. This large use of time increases the cost and complexity of the study and thus the cost to the patient.

The patient's heart rate must also be monitored during the study to help keep stress levels low. Previous methods of determining the heart rate have been relatively slow and inaccurate, limiting the ability to carefully monitor the patient's condition.

Additionally, at times during the study the patient may enter ventricular tachycardia, a life threatening condition where the heart stops pumping blood correctly. This condition should be stopped as quickly as possible. This is generally done by changing the pacing signal timing to approximately 70% of the ventricular tachycardia rate and then controlling the pacing once the system has regained control of the heart. This ventricular tachycardia rate has been difficult to measure previously because the signal appears only on an oscilloscope or as a trace on the paper. The interval must be measured and converted to a form to allow setting the pacing signal rate. This process should occur as rapidly as possible to prevent possible complications, but the current cumbersome technique limits the speed.

Digital oscilloscopes have had the ability to indicate the time between two pointers, but conventionally the pointers have been small symbols which are hard to recognize and have been hard to manipulate

SUMMARY OF THE INVENTION

The system of the present invention provides a means for easily making the necessary time measurements of the various signals monitored for electrophysiological analysis and provides a rapid way to determine patient heart beat interval and ventricular tachycardia interval.

The various amplifier outputs of a conventional electrophysiology unit are connected to a multi-channel analog to digital converter unit. This digital information is then utilized by a computer system. The computer system stores the information on a large capacity storage medium and displays selected signals on a high resolution graphic display. In one mode of operation, the analysis mode, a pair of calipers or bars are displayed on the monitor. A trackball or other pointing device is used to manipulate the calipers. One caliper can be fixed and the other moved, with the time interval between the two bars being displayed between the bars. This allows the physician to rapidly determine the time between desired events. The calipers can be locked at a given opening or time and moved to another portion of the data for comparison purposes. The calipers are digitally locked and the physician need not fear changing the setting while leafing through mounds of paper.

The computer system also monitors a selected channel to determine an event interval, generally the time between heart beats. The computer determines baseline, minimum and maximum values and develops a comparison level, which is a portion of the magnitude of signal amplitude. A timing interval starts when the signal crosses the comparison level and stops when the signal crosses the level again, after a given non-monitored interval. This allows the heart beat interval and the ventricular tachycardia interval to be easily determined. The interval is displayed on the graphic display to allow the attending persons to rapidly determine the pacing settings needed to allow preventative measures to be taken much more quickly.

BRIEF DESCRIPTION OF THE FIGURES

A better understanding of the invention can be obtained when the following detailed description of the preferred embodiment is considered in conjunction with the following drawings, in which.

DETAILED DESCRIPTION OF THE PREFERRED EMBODIMENT

Figure 1:
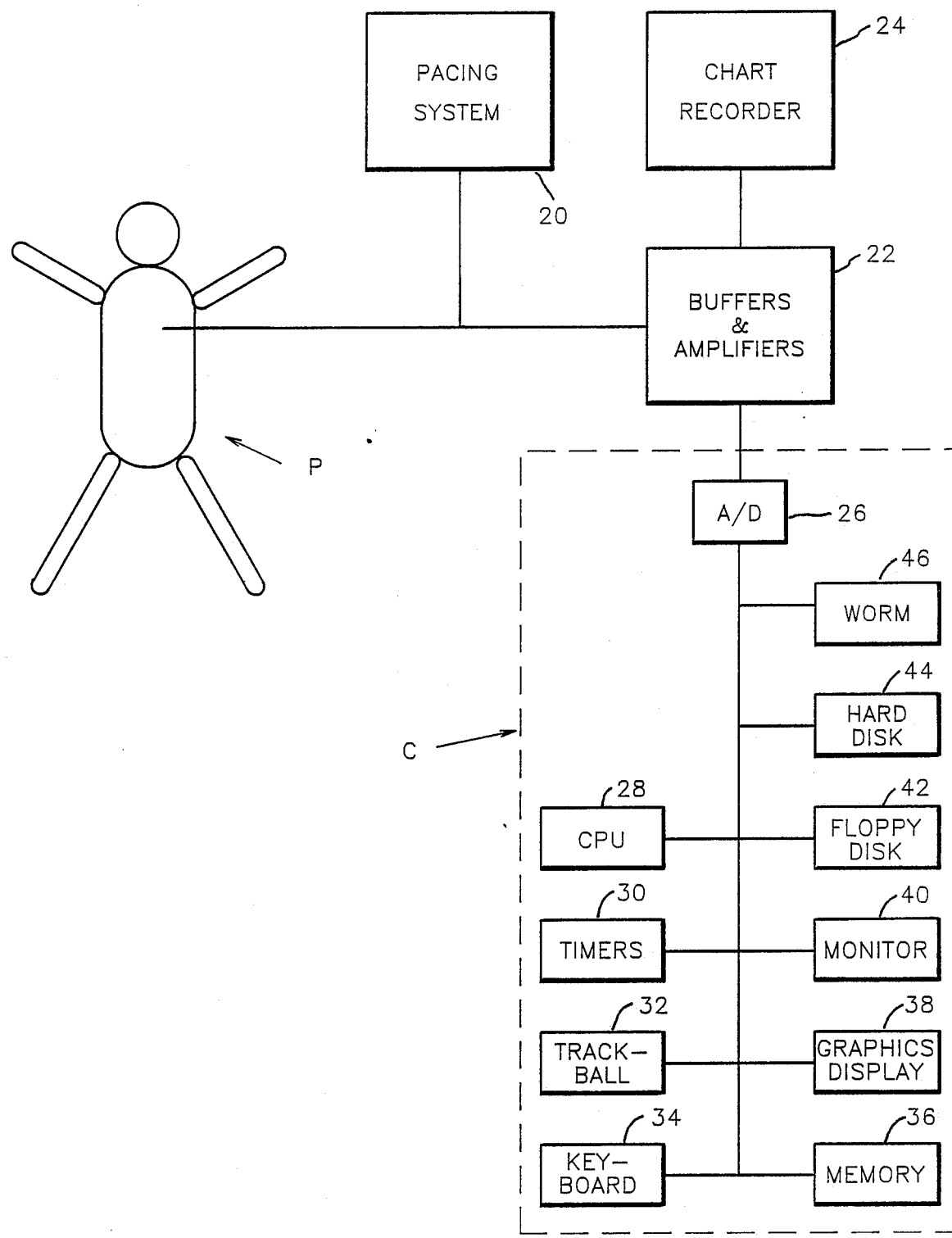
FIG. 1 is a block diagram of a system incorporating the present invention connected to a patient.

Referring now to FIG. 1, a patient, generally referred to by the letter P, is connected to an electrophysiology system. The various catheters and their incorporated electrodes are placed in the heart and connected to a pacing system 20 and a buffers and amplifiers unit 22. The pacing system 20 allows the control of the various signals applied to the heart for study purposes, as discussed in the background of the invention. The buffers and amplifiers 22 provide the amplification necessary to alow simpler signal processing than if the low level signals produced by the heart were used.

The outputs of the buffers and amplifiers unit 22 may be connected to a conventional chart recorder 24 if desired to produce a positive, conventional record of the signals received from the patient P. The output of the amplifiers unit 22 is connected to a computer system c for use according to the present invention.

The computer system incorporates an analog/digital (A/D) converter unit 26 which receives the output signals from the amplifiers unit 22. The analog/digital converter unit 26 provides the necessary circuitry to convert the analog signals to a digital form for use by the computer. The analog signals are sampled at given time intervals, in the preferred embodiment one millisecond, and converted to digital form. The computer system is based on a central processing unit (CPU) 28 and has various connections to a series of associated devices such as a timer module 30, a trackball 32, a keyboard 34, necessary memory 36, a bit-mapped high resolution graphic display 38, may contain a standard computer monitor 40 and contains various storage devices, such as a floppy disk unit 42, a hard disk unit 44 and an optical disk unit 46, preferably an optical disk in the form of a Write Once Read Many disk or WORM.

While a study is underway, the amplified signals are received by the analog to digital converter 26 and provided to the CPU 28 to be stored on the WORM 46. This provides a continuous manner of storing the signal information for later use and analysis. The selected signal information is displayed on the high resolution graphic display 38 to allow real time monitoring of the events being received from the amplifiers unit 22, that is, the events occurring within the heart of the patient P.

The trackball 32 is the primary user control during a study or analysis and has a ball device for input of direction and movement information and has three auxiliary buttons, which have defined uses depending upon the operating sequences being performed by the CPU 28.

Figure 2A:
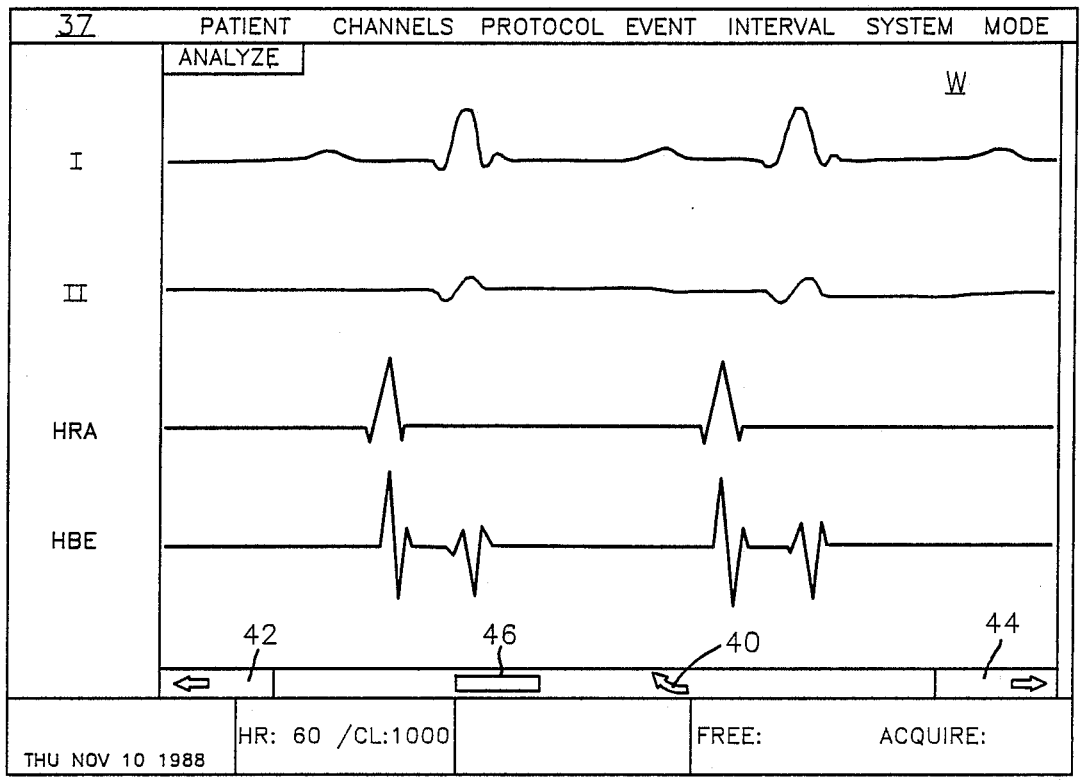
FIGS. 2A, 2B, 2C, 2D, 2E and 2F are illustrations of the graphic displays of the system of FIG. 1, the figures showing various caliper variations.

An example of the information available on the graphic display 38 is shown in FIG. 2A. The display has a number of segments for use in operating the system. For example, across the top is a selection menu line 37 used to select various menus for option and activity selection. A menu is activated by moving the conventional cursor 40 up to that location and selecting the particular type of menu to be selected. The menus pop down and have a list of the options available under that menu. In the particular instance illustrated, the unit or system is in the analyze mode and thus is displaying previously recorded signal data on the graphic display 38. To the left of the displayed data are indicators of the various names or acronyms of the wave forms for use by the physician. Directly below the illustrated wave forms are data movement segments 42 and 44. Between the two data movement segments 42 and 44 is a bar graph 46 illustrating the size of the displayed information with respect to the entire length of the given protocol which is evaluated. At the bottom of the display is an indication of the date, the heart rate and interval of the patient, the remaining time available on the optical disk and the amount of time that has occurred since the beginning of the protocol.

The trackball 32 used in the preferred embodiment has three buttons referred to as the left, middle and right buttons, as well as a movement ball. In the analyze mode the buttons are assigned the functions of anchoring or setting the anchor bar for measurement, entering the comparison mode wherein the two side bars comprising the calipers are fixed in position and the exiting the analyze mode. While a trackball 32 is used in the preferred embodiment, it is understood that other pointing devices such as mice or Joysticks could be utilized.

Figure 2B:
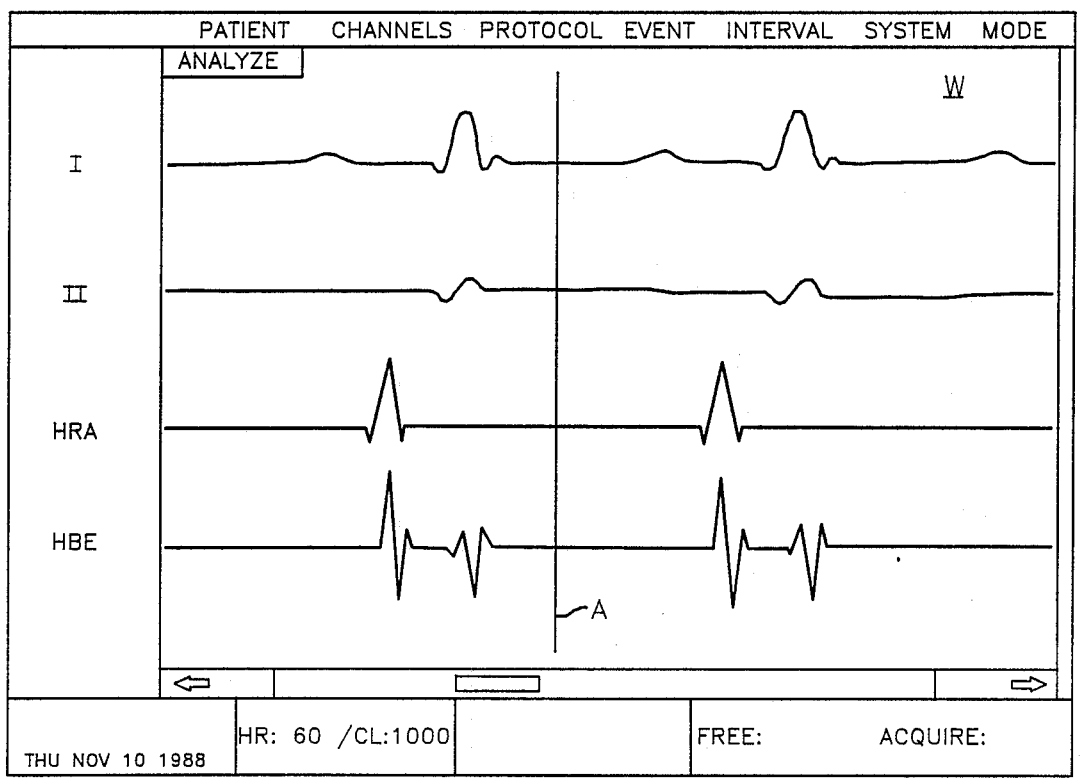
Figure 2C:
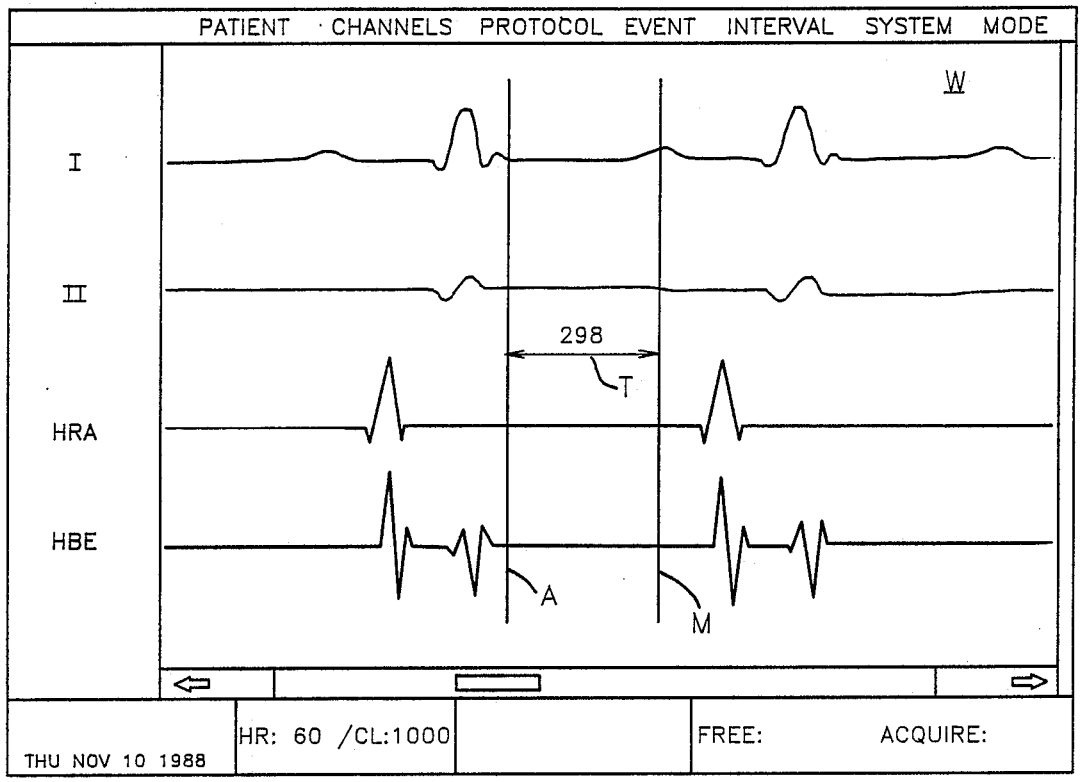

FIG. 2B, the cursor 40 has been moved up into the active window W of the display where the signal waveforms are actually displayed. The left button of the trackball 32 has been pressed and the resulting operation is the presence of a single line or bar A on the window g, which indicates the location of the anchor bar A. The anchor bar A is the reference line from which time value measurements are obtained. The height of the anchor bar A is such that it extends to nearly the limits of the window W. When the ball in the trackball 32 is moved to the right, the display shown in FIG. 2C results. A second bar M, the movable or measurement bar, appears as the trackball 32 indicates horizontal movement. Presented between the two bars A and M is a time line T, with a time value indicated above the line T. The number displayed above the time line T is the time difference between the two bars A and M in milliseconds and is accurate to one millisecond resolution in the preferred embodiment because that is the A/D converter 26 sampling interval. The intersection of the time line T and the movable bar M is the cursor location.

Figure 2D:
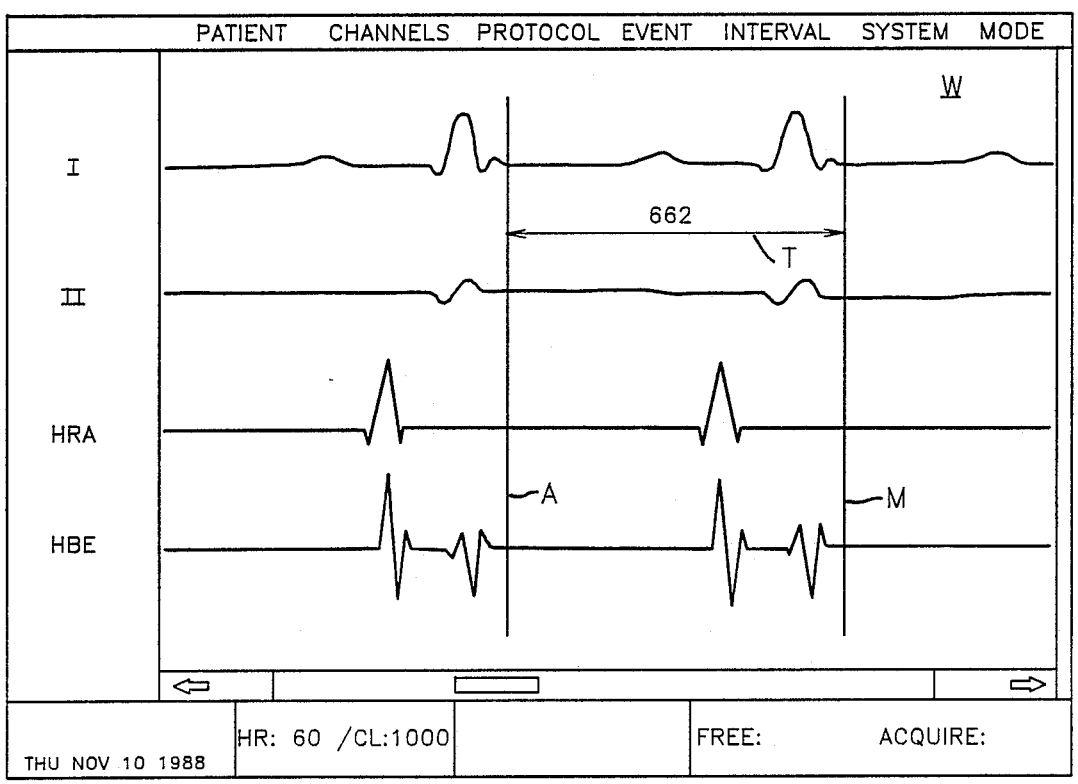

As the trackball 32 is rolled further to the right, the movable bar M moves further to the right. For ease of reference, it is understood that a reference to the trackball 32 moving in a given direction is a reference to moving the ball in the trackball 32 in that direction. The trackball 32 mag also be moved in a vertical direction, which causes the location of the time line T to move vertically in the display. In the case shown in FIG. 2D, the trackball 32 has been moved to the right and vertically, so that the movable bar M is moved further right, there is now a time interval displayed of 662 milliseconds between the two bars A and M and the time line T has moved vertically to between the I and II waveforms. The physician need only place the anchor bar A where desired and move the movable or measurement bar M as desired, reading the time interval value from its position above the time line T to make measurements.

Figure 2E:
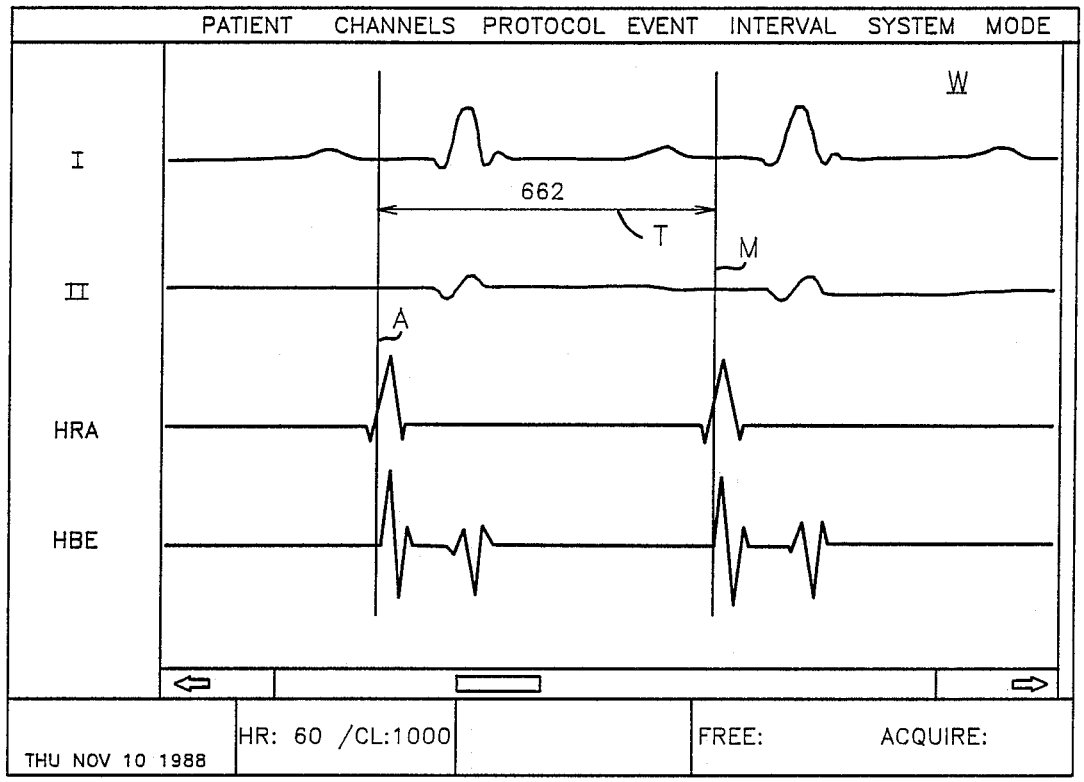

If the middle button on the trackball 32 is then depressed, the two bars A and M which form the calipers, are locked in relative position to each other. The trackball 32 is then moved to the left and the display of FIG. 2E results. The interval between the two bars A and M has not changed and both bars A and M have moved to the left to allow proper timing of an interval. Thus in this locked or compare mode it is possible to set the calipers or bars A and M a fixed distance apart with the interval value displayed above the time line T, and move this caliper setting as desired, to allow quick and accurate comparisons of the various events which have occurred in the study. If the second event does not line up with the calipers, the trend and difference can be determined.

Figure 2F:
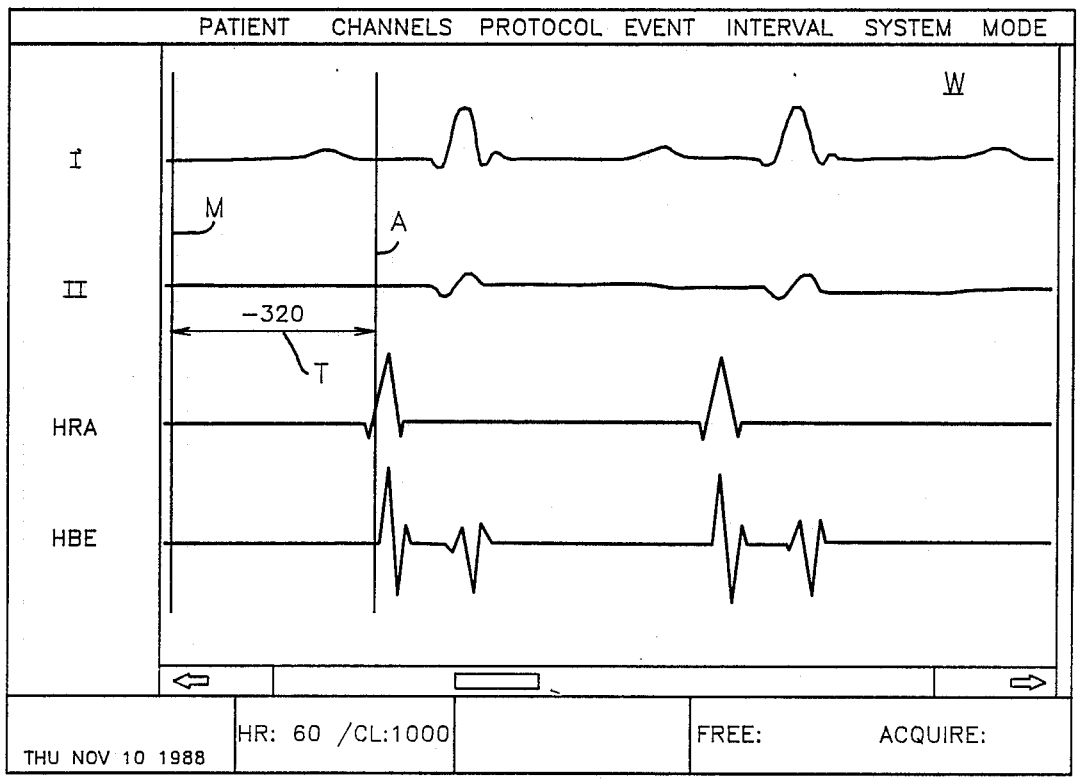

In FIG. 2F the anchor bar A has been reset by hitting the left button on the trackball 32 and the trackball 32 has been rolled to the left so that the movable bar M is to the left of the anchor bar A, with the resulting negative time interval displayed. The movable bar M is very close to the left edge of the window W. The window W has a narrow band along its side boundaries so that if either of the bars A or M enter this region, the signal information contained in the window W is panned, thus eliminating the need to actually move down below the window W and use the screen control functions.

The use of the trackball 32 and the calipers of the present invention is relatively easy and allows a physician to rapidly gather the timing information necessary in electrophysiology studies to determine the various problems with the individual patient's heart.

Figure 3A:
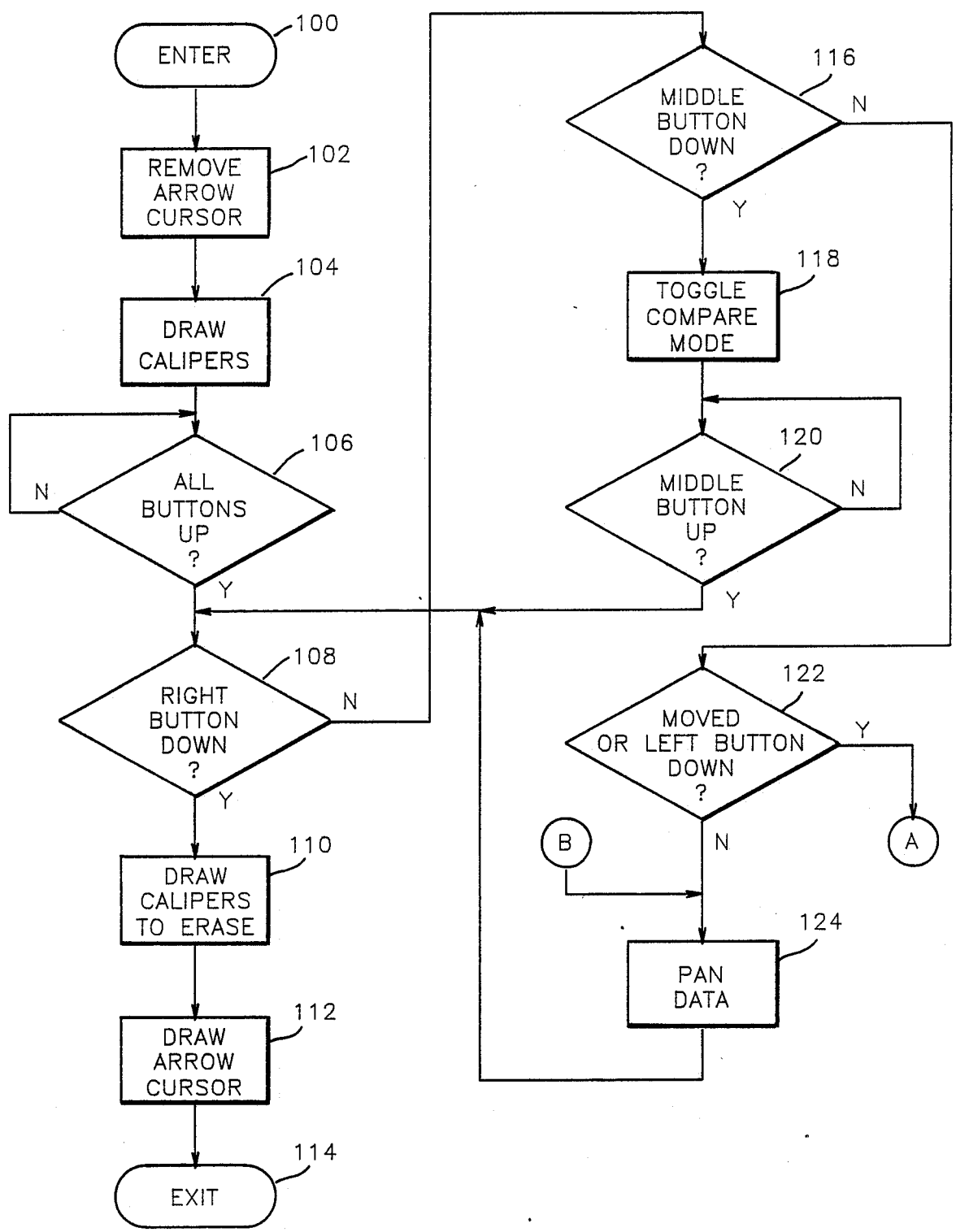
FIGS. 3A, 3B, 3C, 4A, 4B, 5 and 6 are flowchart illustrations of operating sequences for developing calipers according to the present invention

The caliper control sequence 100 is entered at step 102 (FIG. 3A). The cursor location is assumed to be within the window position W upon entry because the analyze mode is entered from a pop down menu overlapping the window W. In step 102 the computer system c removes the arrow cursor from the screen and then in step 104 proceeds to draw the calipers using the draw calipers sequence 300, which will be discussed in more detail. The computer system c then waits until all buttons on the trackball 32 are up in step 106. After all the buttons have been released, the computer system c then determines if the right button has been depressed. If it has been depressed, this is an indication to exit the analysis mode, and control proceeds to step 110 where the computer system C draws the calipers again to erase them and then in step 112 the computer system C proceeds to draw the arrow cursor 40 to commence alternate action and menu selection capabilities. The caliper control sequence 100 is then exited in step 114.

If the right button had not been depressed, indicating that analysis mode was not terminated, control proceeds to step 116 where the computer system c determines whether the middle button is down, indicating that the compare mode is to be changed. If the compare mode is to be changed, control proceeds to step 118 where the compare mode is toggled. If the computer system C was in compare mode, hitting the middle button cancels this mode and the movable bar M is free to move relative to the anchor bar A. If the computer system C was not in compare mode, compare mode is entered and the calipers are looked and control proceeds to step 120. In step 120 the computer system c waits for the middle button to be raised at which time control proceeds to step 108 and processing of the loop is continued. If the middle button was not depressed, control proceeds from step 116 to step 122 where the computer system c determines whether the trackball moved or whether the left button is depressed. If neither operation is true, the computer system proceeds to step 124 where the pan data sequence 400 is called to pan the displayed signal data if necessary.

Figure 3B:
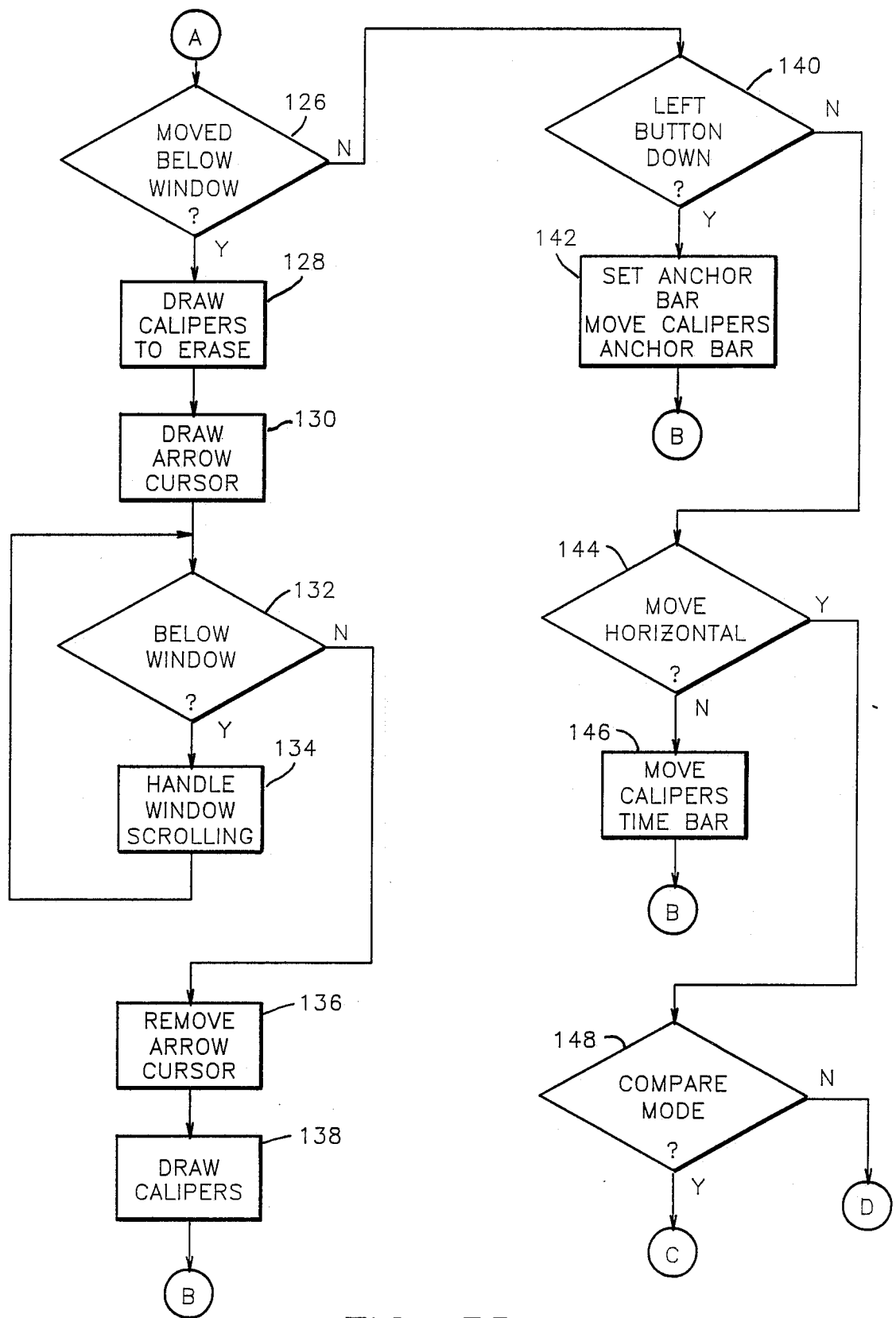

If the trackball 32 had been moved or the left button is depressed, control proceeds from step 122 to step 126 (FIG. 3B). In step 126 a determination is made as to whether the cursor has moved the position below the window W. If so, this is an indication that the physician would like to pan the data in a rapid fashion. Therefore in step 128 the draw calipers routine is called to erase cursor 40 is presented in the proper position below the window W. In step 132 a second check is made to see if the cursor position is still below the window W. If so, control proceeds to step 134 where the various window scrolling functions are performed. These are performed by having the trackball 32 moved to the left or right to the various arrow positions indicated and depressing a button to cause the entire window W to be scrolled as desired. After the particular scrolling function has been completed, control returns to step 132 to see if the cursor position has moved and is still below the window. If the arrow cursor 40 has left the portion below the window used for scrolling functions, this is an indication that the physician washes to reenter analysis mode in the particular screen displayed and therefore control proceeds from step 132 to step 136 where the arrow cursor 40 is removed and then to step 138 where the calipers are redrawn on the window W. Control then proceeds from step 138 to step 124 to pan the data if necessary.

If the cursor position had not moved below the window W, control proceeds from step 126 to step 140, where a determination is made as to whether the left button has been depressed. Depression of the left button in analysis mode is an indication that the anchor bar A is to be set at the cursor location and coupled to the data present at that location. Therefore, in step 142 the computer system C sets the anchor bar A at the cursor position to allow measurements to commence and calls the move calipers sequence 200 with the anchor bar as the argument or intended gag to be moved. Control then proceeds to step 124 to pan the data if necessary.

If the left button was not depressed, control proceeds from step 140 to step 144, where a determination is made as to whether the cursor moved horizontally. If the cursor did not move horizontally, but moved merely vertically, then step 144 transfers control to step 146 where a call to the move calipers sequence 200 is made with an argument that the time bar is to be moved as necessary. After step 146 is completed, control proceeds to step 124 to pan data if necessary.

Figures 3C, 4A:
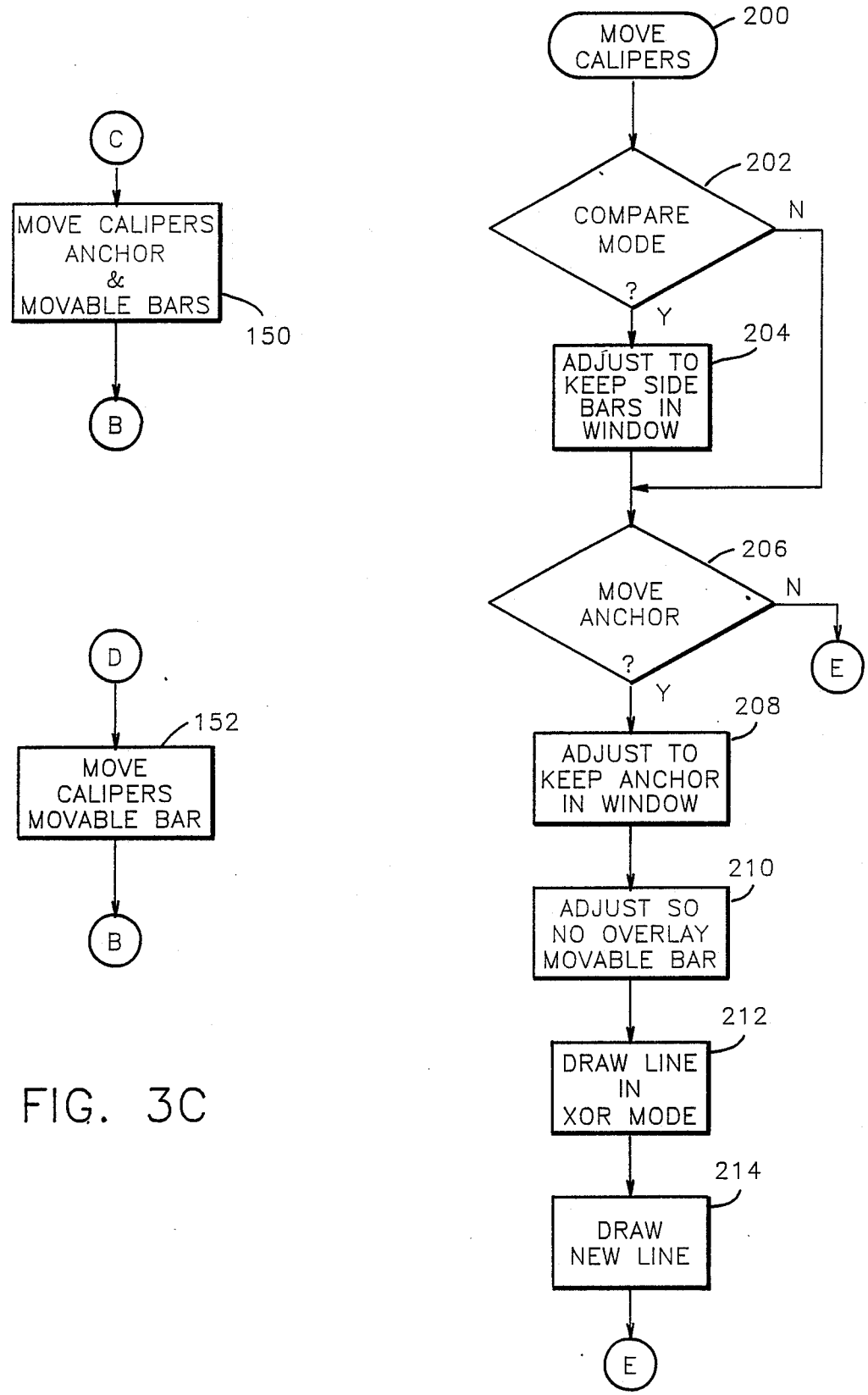

If a horizontal movement of the cursor and the trackball 32 was present, step 144 transfers control to step 148, where a determination is made to see if the computer system C is in the compare mode. If the compare mode is active, control proceeds from step 148 to step 150 (FIG. 3C). In step 150 the move calipers sequence 200 is called, with an indication that both the anchor and movable bars are to be moved. Control proceeds from step 150 to step 124 for data panning. If the system was not in compare mode, that is the two bars A and M were not locked in a fixed relationship, then oontrol prooeeds from step 148 to step 152, where a call to move calipers sequence 200 is made, with the movable bar as an argument. Control proceeds from step 152 upon return from move calipers sequence 200 to step 124, where the data is panned if necessary.

The move calipers sequence 200 (FIG. 4A) commences at step 202. A determination is made as to whether the computer system C is in the compare mode. If the system is in the compare mode, control transfers to step 204 where the desired movement of the caliper pair, as indicated by the trackball 32, is adjusted so that neither of the side bars move outside the window W. For example, of the trackball motion had been very great, indicating a large motion, then this motion would, if properly and directly correlated, move one of the bars A or M off of the window W, this movement is reduced to the proper value to keep the bar A or M on the window W. After this adjustment is made in step 204, or if the computer system C was not in compare mode, control transfers to step 206, where a determination is made based on the arguments received by the move calipers sequence 200 as to whether the anchor bar A is to be moved.

Figure 4B:
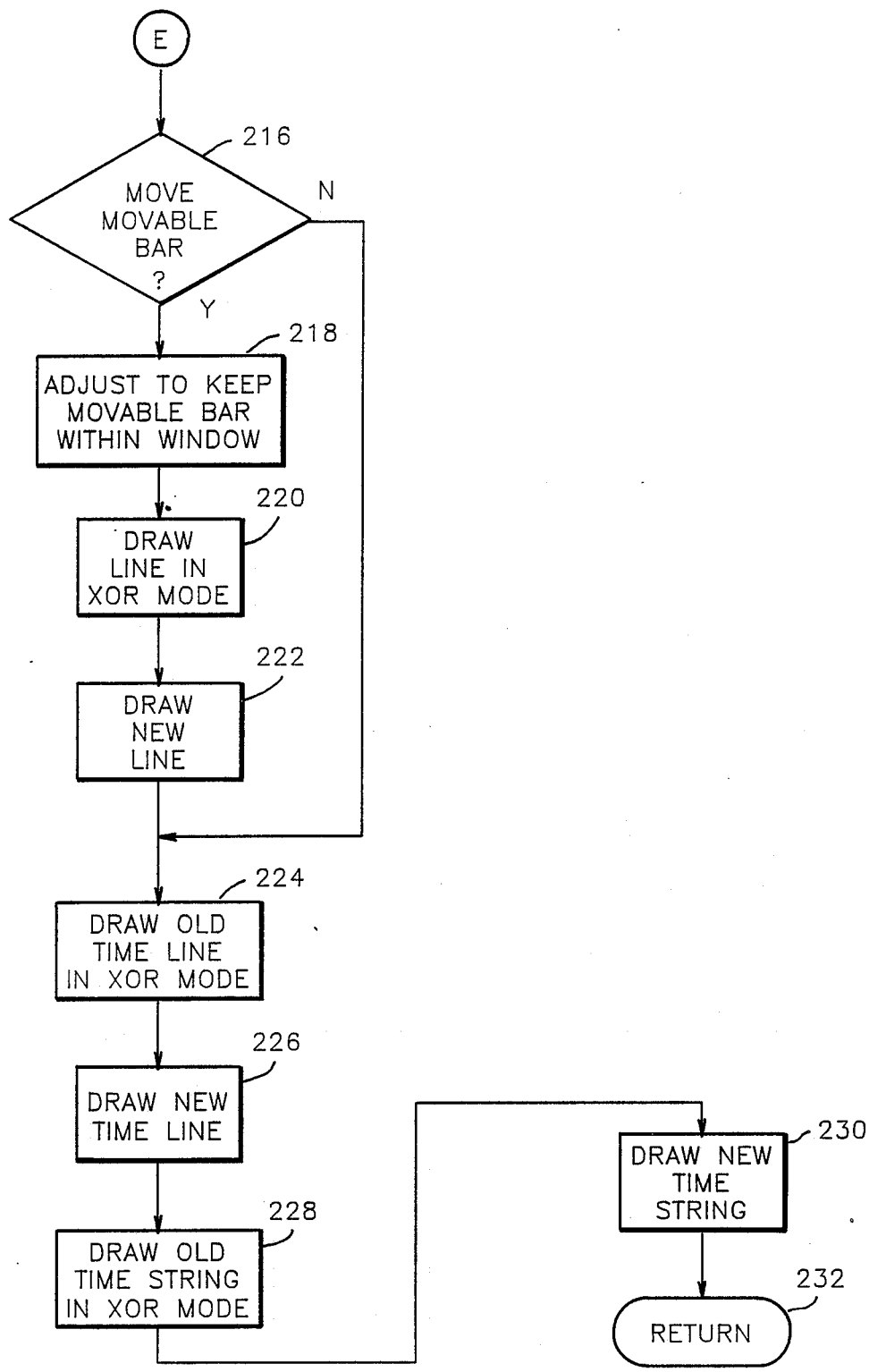

If the anchor bar A is to be moved, control proceeds to step 208 where an adjustment is made to the desired movement to keep the anchor bar A within the window W. If this step is performed after step 204, no adjustment is necessary because the adjustments would have been completed in step 204. Control then proceeds from step 208 to step 210, where an adjustment is made so that the movable bar M is not overlayed by the anchor bar A. This is so that the physgcgan can determine the position of the two bars A and M. In step 212, the step following step 210, the anchor bar A is drawn in XOR mode so that any of the existing data present underneath the current location of the anchor bar A is retained and the current anchor bar A is removed. In step 214 a new line or anchor bar A is drawn at the new position this operation also being done in XOR mode so that the line is highly visible and can be easily erased. After the completion of the new anchor bar A, control proceeds to step 216 (FIG. 4B), which is also where control proceeds if the anchor bar A was not to be moved.

In step 216 the computer system C checks to see if the movable bar M is to be moved. If so, control proceeds go step 218 where an adjustment is made to keep the movable bar M within the window W. Control then proceeds to step 220, where the existing movable bar M is drawn in XOR mode to erase it from the display. Control then proceeds to step 222 where a new line forming the movable bar M is drawn at the proper location.

Control then proceeds to step 224 from step 222 or from step 216 if the movable bar M is not to be moved. Step 224 commences an operation wherein a new time line T and new time value are displayed. The time value and time line T are rewritten anytime either the anchor bar A or the movable bar M are moved or whenever the trackball 32 is moved vertically. In step 224, the old time line T is drawn in XOR mode to erase it from the display. In step 226 a new time line T is drawn. In step 228, the next step, the old time string is drawn in XOR mode to remove the time value indication from the display and in step 230 the new time string is drawn, to indicate the new time interval between the calipers, that is, between the anchor bar A and the movable bar M. After completing step 230, control proceeds to step 232 which is a return operation to the calling sequence.

Figure 5:
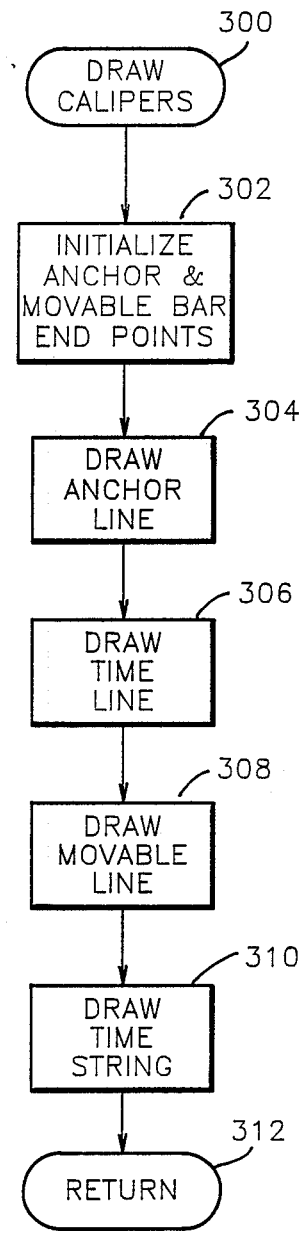

The draw calipers sequence 300 (FIG. 5) is commenced at step 302, where the initial anchor and movable bar end points are determined. This initializes the height of the two lines based on the vertical size of the window W. Control then proceeds to step 304 where an anchor bar A is drawn on the display. Following the completion of the drawing of the anchor bag A, control proceeds to step 306 where the time line T is drawn and to step 308 where the line representing the movable bar M is drawn. Following this, in step 310 the time string is drawn above the time line T, thus completing the drawing of the calipers on the display. The draw calipers sequence 300 is utilized only when the calipers are to be drawn to the display, or erased from the display, not when the calipers are to be moved. The operations are performed in XOR mode to improve contrast and to ease erasure. After completing the drawing of the time string in step 310, control proceeds to step 312, which is a return to the operating sequence.

Figure 6:
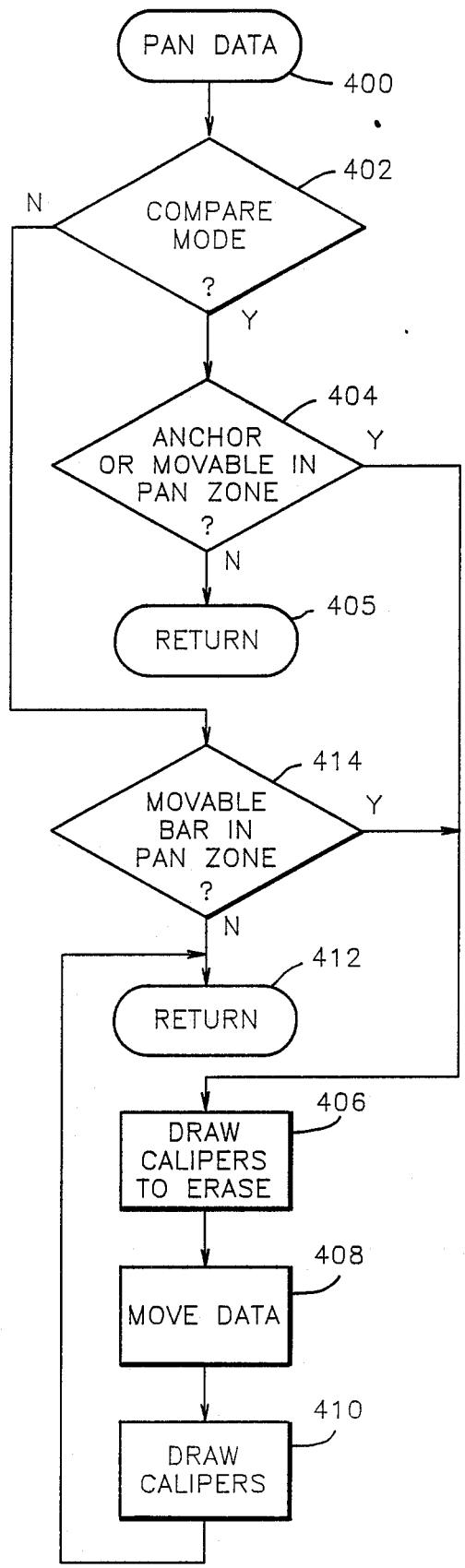

The pan data operation performed in step 124 is accomplished by a call to the pan data sequence 400. The pan data sequence 400 (FIG. 6) starts in step 402 by determining whether the computer system C is in the compare mode. If the system is in the compare mode, control proceeds to step 404 where a determination is made to see if either the anchor bar A or the movable bar M are within the pan zone. The pan zone is a zone near the ends of the window W, in the preferred embodiment a five pixel zone, into which should the bars move, it will cause panning of the displayed signal data. This panning allows the physician to move data without the need to go below the window W and operate the scrolling commands. The physician just moves a bar A or M to the end of the window W and panning proceeds until the bar A or M is out of the pan zone. If the physician keeps moving the bar A or M into the pan zone, the signal data can be scrolled as desired.

If the anchor bar A or the movable bar M are not within the pan zone, then control proceeds to step 405, which is a return to the calling sequence. If either of the bars A or M is within the pan zone, step 404 transfers control to step 406, where a call to the draw calipers sequence 300 is made to erase the existing calipers from the screen. The erasure happens because the draw calipers routine always operates in the XOR mode and thus a redrawing of the calipers erases the calipers. Control then proceeds to step 408 where the signal data presented on the display is moved and redrawn, thus panning the data. Control proceeds to step 410 where a call to the draw calipers sequence 300 is made to redraw the calipers at the same position relative to the data. Control then proceeds to step 412 which is a return to the operating calling sequence.

If the computer system c was not in the compare mode in step 402, control transfers from step 402 to step 414, where a determination is made to see if the movable bar M is in the pan zone. If not, control proceeds to step 412, a return to the calling sequence. If so, control proceeds to step 406 and the calipers are erased and redrawn and the data moved as necessary as previously discussed. The location of the anchor bar A is not checked and because the anchor bar A is tied to the data, the anchor bar A can move off the window W, thus allowing a time greater than the width of the window W to be measured.

Thus, using the computer system c utilizing the present invention, a physician can easily measure the time between two points on the displayed electrophysiological data obtained during a study of the patient. The physician need not use the mechanical calipers as in a conventional study and thus the possibilities of inaccuracy are greatly reduced and the speed of the operation is improved.

Figure 7:
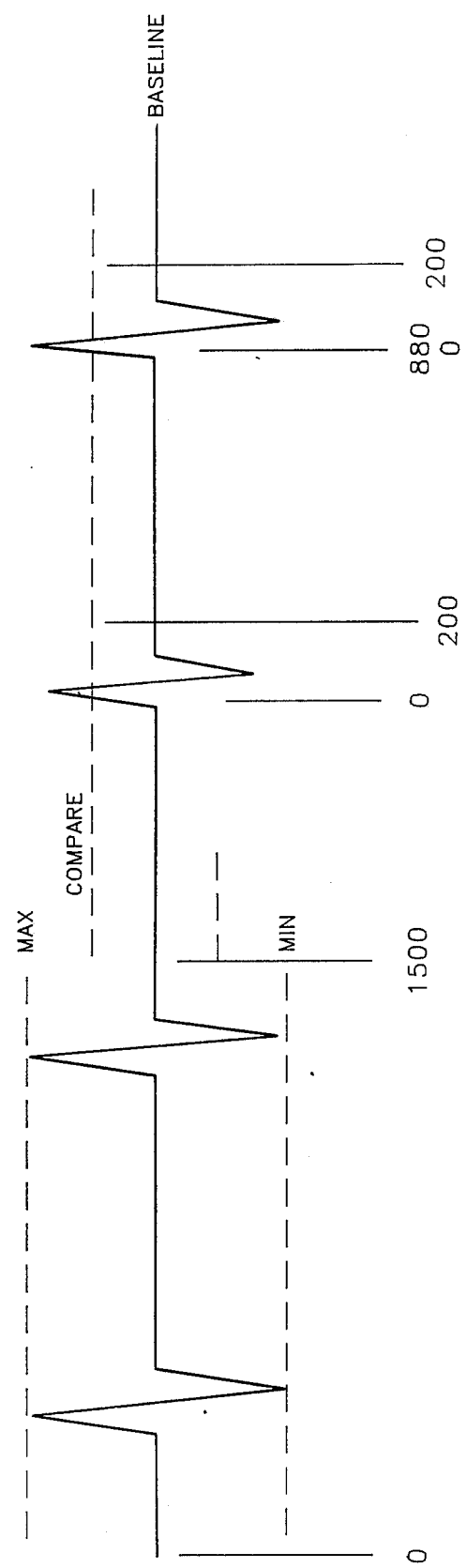
FIG. 7 is a waveform illustration of an intracardial signal used to monitor heart rate.

The computer system C of the preferred embodiment also automatically determines and displays the time between certain events of a specified channel. For example, as shown in FIG. 7, a given wave form is presented on a channel to the system. This channel is specified to the computer system c to be the channel used to determine the heart rate and interval of the patient. The signal conventionally used has a wave form similar to that as shown in FIG. 7, having maximum and minimum values of the signal, having a baseline value that is approximately a zero value, and having relatively steep and clean signal transitions due to the inherent signal characteristics and filtering that has been done by the amplifiers unit 22.

Figure 8A:
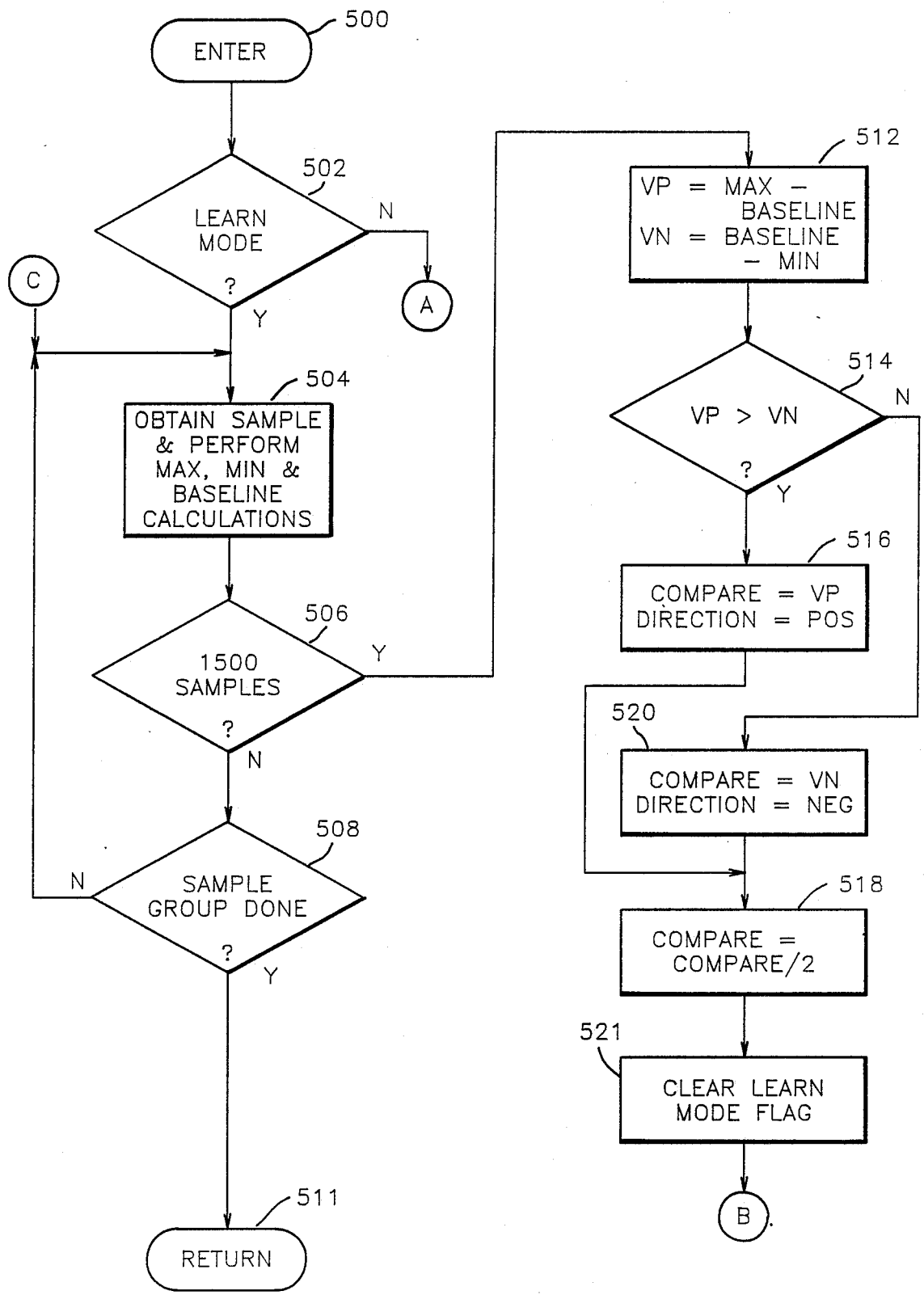
FIGS. 8A, 8B and 8C are flowchart illustrations of the method for determining event intervals.

Determination of the heart rate is commenced in the heart rate sequence 500 at step 502 (FIG. 8A). In step 502 the computer system C determines whether the heart rate determination is in the learn mode, indicating that various initialization parameters, that is the maximum, minimum and baseline values, as shown in FIG. 7, have not been determined. If it is in learn mode, this is an indication that new parameters need to be determined. Control thus proceeds to step 504 where a sample value is obtained. Data is passed to this routine, which is an interrupt driven routine in groups of 32 samples contained in a buffer or queue which have been gathered by other portions of the operating sequences (not shown) of the computer system C. Each sample represents the signal level at a given point in time, each sample being one millisecond apart in the preferred embodiment. In step 504 the computer system C obtains a sample from this queue and performs the maximum, minimum and baseline calculations. The maximum calculation is simply a determination as to whether the value of the particular sample is the greatest it has obtained during this interval. If so, this value is saved for later use. Minimum calculation is similar in that the minimum values are obtained.

The baseline calculations can be determined in any of three ways. The preferable method is to wait until a 150 millisecond interval has passed after a given signal peak value. The next three sample values are averaged. The 150 millisecond value is chosen because this is time where a normal heart beat would not develop and thus, the signal should be at a quiescent or baseline level.

The second method for determining the baseline value is to take a rolling average of all the samples obtained. This is not as desirable because this is a more complicated routine which takes more time, and because this is a real time system, fast methods for determining the baseline value are desirable.

A third method is to take a number of samples, for instance 100 samples, and discard all of those samples which are not within a given dead band or tolerance of another series of samples. In this way, any peak or minimum values would be discarded and only values around the baseline value would remain. This is based on the principle that the baseline value occurs on the desired channel with the greatest frequency and therefore all other signals will be discarded.

When the maximum, minimum and baseline calculations have been performed in step 504, control proceeds to step 506 where a check is made to see of 1500 samples have been analyzed. A 1500 sample interval is selected because this is approximately 1.5 seconds in the computer system C of the preferred embodiment where the sample interval is one millisecond. At least one heart beat should have occurred during this 1.5 second period and therefore these should be at least one valid interval to obtain the maximum, minimum and baseline values. If the 1500 samples have not been completed, control proceeds to step 508, where a determination is made as to whether the last sample in the group has been obtained. If not, control proceeds to step 504 and the calculations are performed on the next sample. If this is the last sample in a group, control returns in step 511 from this interrupt routine to the interrupted routine for further processing.

If 1500 samples have been completed, control transfers from step 506 to step 512 where the maximum and minimum values are compared against the baseline to determine the pulse heights of the signal data that has been sampled. For example, a value called VP is determined by subtracting the baseline value from the maximum value and a value VN is obtained by subtracting the minimum value from the baseline value. Thus, a positive value is obtained to indicate the maximum pulse height in either direction.

The two VP and VN values are then compared in step 514. If the VP value is greater, indicating that the positive going pulse had a greater magnitude than the negative going pulse, then control proceeds to step 514 where a value called COMPARE is set at the VP value and a direction indicator is set as positive. Control then proceeds from step 516 to step 518. If the VN value was greater than the VP value, control proceeds to step 520 where the COMPARE value is set at the VN value and the direction pointer is indicated as being negative. Control then proceeds to step 518. Thus, the COMPARE value is always positive and is the greater of the two deviations from the baseline. In step 518 the COMPARE value is divided by 2 for a basis for determining the start of an event. The computer system C is now ready to leave the learn mode and the learn mode flag is cleared in step 521.

Figure 8B:
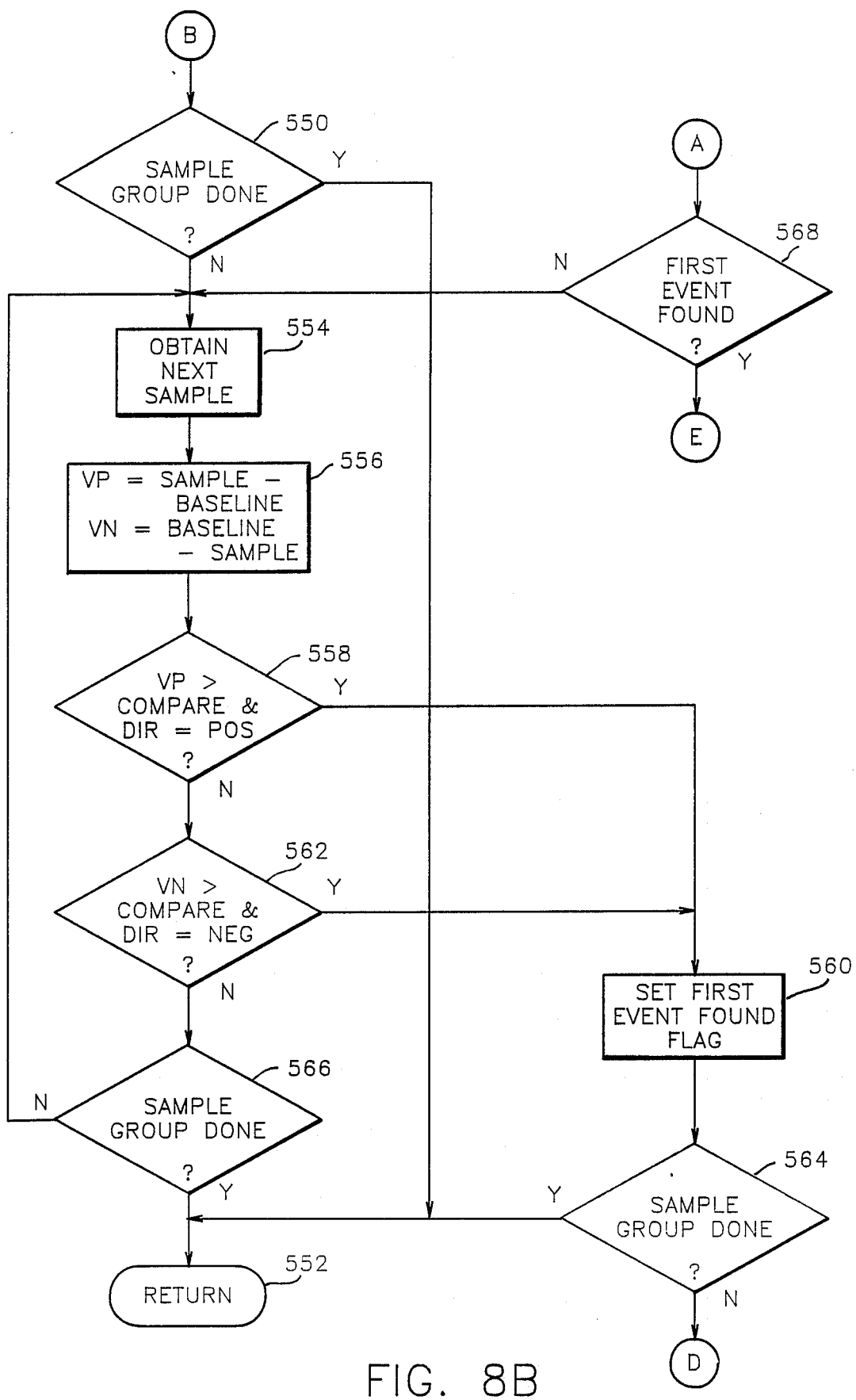

From step 521 control proceeds to step 550 (FIG. 8B), where a determination is made if this is the last sample in the group. If it is, control proceeds to step 552 where control returns to the interrupted routine.

Figure 8C:
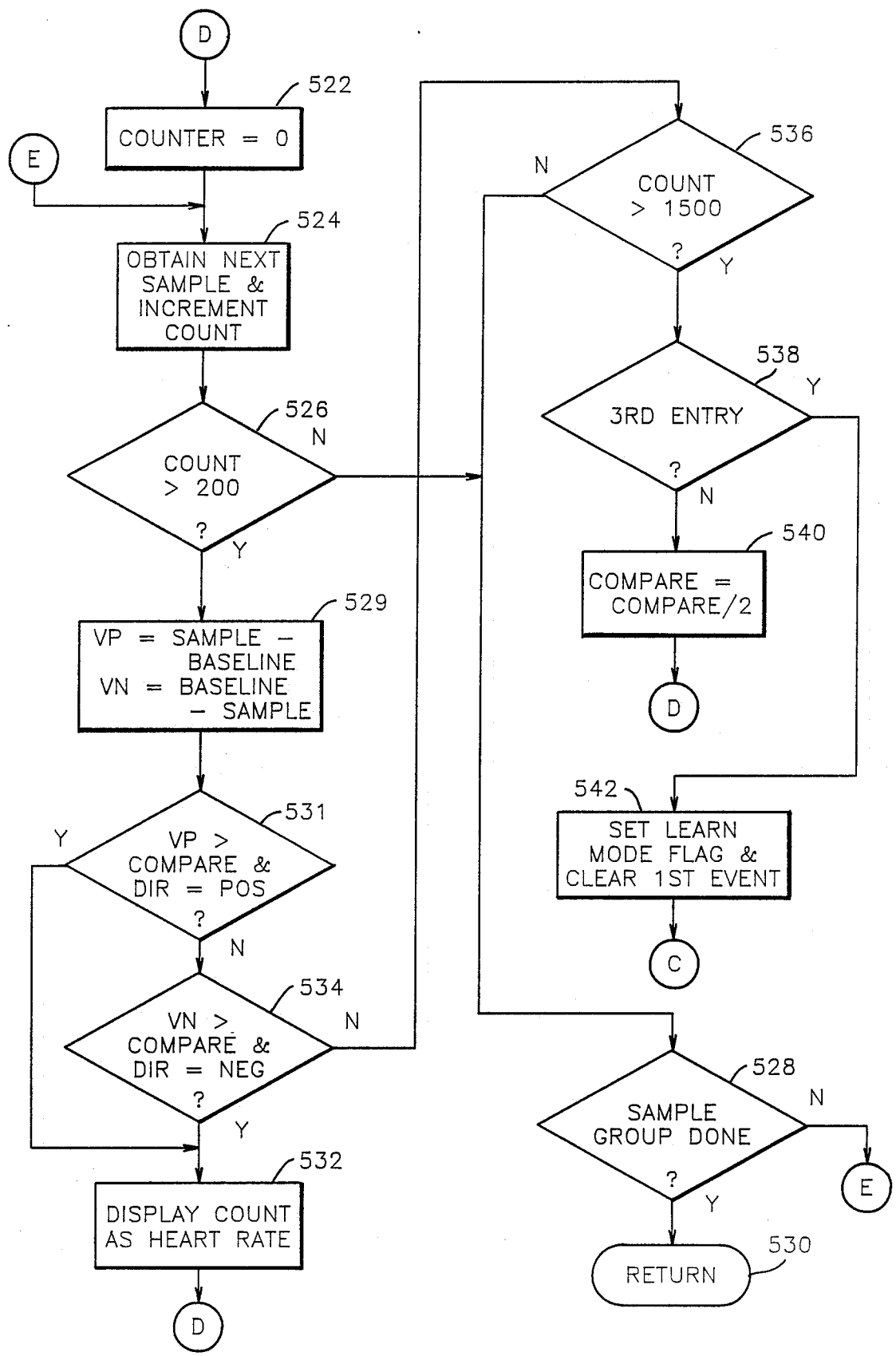

If there are more samples, the computer system C proceeds to obtain the next sample in step 554. In step 556 a VP value is developed by subtracting the baseline from the sample value and a VN value is developed by subtracting the sample value from the baseline. Next, in step 558, a determination is made by the computer system C if the VP value is greater than the reference level, the COMPARE value, and if the direction is positive. If so, control proceeds to step 560. If not, control proceeds to step 562, where the VN value is compared to the COMPARE value to determine if it is greater and a check is made to determine if the direction is negative. If so, control proceeds to step 560 where the first event found flag is set indicating that the first heart beat has been found. This allows only proper data to be displayed and not an initial erroneous value, followed by proper values. Control then proceeds to step 564, where a determination is made whether the sample group is done. If so, control returns to the interrupt routine in step 552. If not, control proceeds to step 522. In step 522 (FIG. 8C), a counter, which is used to indicate the heart rate interval, is set to zero. Control then proceeds to step 524.

If the result of either of the comparisons of step 562 was negative, control proceeds to step 566 where a determination is made if the sample group is done. If not, control proceeds to step 552 and to the interrupted routine.

If in step 502 the computer system C determines that the system is not in learn mode, control proceeds to step 568, where a determination is made if the first event has been found. If not, control proceeds to step 554 to proceed in finding the first event. If the event has been found, control proceeds to step 524.

In step 524 the next sample in the sample group is obtained and the count value is incremented. Control then proceeds to step 526 where a determination is made to see if the count value is greater than 200. Because this technique is looking for the next event or sample representative of a heart beat having an amplitude greater than the compare value, it is undesirable, based on the data being obtained, to trigger within any given refractory or delay period. This value is set to be 200 so that any aberrations in the data as the heart settles down from the pacing done in the study do not cause triggering of the heart rate interval and the triggering occurrs only the first time the signal level exceeds the compare value. Therefore, if the count is not greater than 200 control proceeds from step 526 to step 528. In step 528 the computer system C determines if the sample group is completed. If not, control proceeds to step 524 for incrementing of the count value and determining the next sample. If the sample group is completed, control proceeds to step 530 which is a return from the routine.

If the count was greater than 200, then control proceeds from step 526 to step 529, where a value VP is developed which is the sample amplitude value minus the baseline value, and a VN value is obtained, which is the baseline value minus the sample value. These are then respectively the positive and negative amplitudes in comparison to the baseline value. Control then proceeds to step 531 where a determination is made if the VP value is greater than the compare value and the direction of the reference pulse is positive. It this condition is met, this is an indication that a timing or second heart beat has occurred and therefore the count value is the interval value. If the condition is meg, control proceeds from step 531 to step 532, where the count value is displayed on the display as the interval and the heart rate is computed from the interval and displayed. Thus, the physician is presented a display which illustrates the heart rate in beats per minute and the interval in milliseconds. Should the system or patient enter ventricular tachycardia, the system of the present invention determines the timing interval between the beats of the heart in tachycardia, and it presents this interval directly on the display. It is then very easy for the physician to indicate this interval to the technicians operating the pacing unit 20, so that the desired interval between pacing beats can be set to terminate the tachycardia condition. Control proceeds from step 532 to step 522 where the counter is zeroed to indicate that a new event sequence is commencing.

If in step 530 it is determined that the VP value is not greater than the compare value and the direction is not positive, control proceeds to step 534 where determination is made to see whether the VN value is greater than the compare value and whether the desired reference pulse direction is negative. If so, ghis indicates that the sample has also triggered an event and control proceeds to 532 for indication of the heart rate and interval. If the test of 534 is also not true, indicating that an event has not been triggered, control proceeds to step 536 where a determination is made to see if the count value is greater than 1500. As previously referenced, a heart beat should occur within a 1.5 second period and therefore if the count is greater 1500 there is some difficulty and various changes have to be made. If the count is not greater than 1500, control proceeds to step 528 for continuation of the routine.

If the count is greater than 1500, control proceeds to step 538 where a determination is made to see if this is the third entry into step 538. If this is not the third entry into step 538, control proceeds to step 540 where a compare value is divided by two and control proceeds to step 522 to reinitialize an event interval. The check for the third entry in step 538 is such that by this time, if it is true, the maximum learned sample deviation would have been divided by eight to act as the compare value. Several divide by two stages are used because the signal voltage reduces during tachycardia or because the catheter may become partially dislodged. However, if the data has to be divided by more than eight before an event is detected, it is determined to be erroneous and therefore it is necessary to restart the learning sequence, where the data is again sampled to determine new maximum, minimum and baseline values. Therefore if this is the third entry, control proceeds from step 538 to step 542 where the learn mode flag is set and the first event found flag is cleared and control proceeds to step 524 where further samples are obtained and the baseline, maximum and minimum calculations are performed.

Thus, this sequence is a relatively quick manner for determining the heart rate interval and displaying this interval and the heart rate on the display for rapid determination and analysis by the physician. The display would also be indicate the entry into ventricular tachycardia and therefore the display would quickly allow the attending technicians and physicians to change the pacing rate to cause the tachycardia to cease and the patient to enter normal rhythms again.

The foregoing disclosure and description of the invention are illustrative and explanatory thereof, and various changes in the size, shape, materials, components, circuit elements, wiring connections and contacts, as well as in the details of the illustrated circuitry and construction and operation and sequence of control may be made without departing from the spirit of the invention.

What is claimed is:

1. A system for measuring time intervals between two locations of an electrical analog signal sampled at a given time interval and converted to digital form, comprising:

means for displaying a portion of the sampled signal in a display window;

means for displaying a reference bar in said sampled signal display window at a location and associating a time of a displayed sampled signal with said location;

means for displaying a measurement bar in said sampled signal display window at a location and associating a time of a displayed sampled signal with said location;

means for a user to indicate desired movement of said measurement bar or said reference bar along said displayed sampled signal;

means for displaying the time interval between said reference bar and said measurement bar; and means for moving said measurement bar in response to said desired movement indication means.

2. The system of claim 1, further comprising:

means for locking said reference bar and said measurement bars in a fixed relationship;

means for moving both said bars in response to said desired movement indication means.

3. The system of claim 2, further comprising:

means for changing the portion of the sample signal displayed in said sampled signal display window when said reference bar or said measurement bar is within a given distance from an edge of said sampled signal display window.

4. The system of claim 1, further comprising:

means for changing the portion of the sampled signal displayed in said sampled signal display window when said measurement bar is within a given distance from an edge of said sampled signal display window.

5. The system of claim 1, wherein said means for displaying the time interval includes displaying a horizontal line connecting said reference bar and said measurement bar and displaying a string of numeric character is located adjacent said horizontal line indicating the time interval.

6. The system of claim 1, further comprising:

means for limiting the location of said reference and measurement bars to within said sampled signal display window.

7. The system of claim 1, further comprising:

means for limiting the location of said measurement bar to within said sampled signal display window.

8. The system of claim 1, further comprising:

means for setting the location of said reference bar in said sampled signal display window.

* * * * *